United States Patent [19]

Daifotis et al.

[11] Patent Number: 5,616,571
[45] Date of Patent: Apr. 1, 1997

[54] BISPHOSPHONATES PREVENT BONE LOSS ASSOCIATED WITH IMMUNOSUPPRESSIVE THERAPY

[75] Inventors: Anastasia G. Daifotis; Ashley J. Yates, both of Westfield, N.J.

[73] Assignee: Merck & Co., Inc., Rahway, N.J.

[21] Appl. No.: 471,466

[22] Filed: Jun. 6, 1995

[51] Int. Cl.$^6$ .................................... A61K 31/66
[52] U.S. Cl. .................... 514/102; 514/103; 514/104; 514/107; 514/108
[58] Field of Search ................................. 514/108, 102, 514/103, 104, 107

[56] References Cited

U.S. PATENT DOCUMENTS 4,870,063  9/1989  Benderup et al. .................. 514/79

OTHER PUBLICATIONS

Hay, J. E. Bone Disease In Liver Transplant Recipients Gastroenterology Clinics of North America vol. 22, Jun. 1993, pp. 337–349.

Fleisch, H. Bisphosphonates: A New Class of Drugs in Diseases of Bone and Calcium Metabolism Recent Results in Cancer Research, vol. 116, 1989 pp. 1–28.

Lukert, B. P. et al. Glucocorticoid–Induced Osteoporosis, Rheumatic Disease Clinic of North America vol. 20, Aug. 1994, pp. 629–650.

Primary Examiner—Theodore J. Criares
Attorney, Agent, or Firm—Joanne M. Giesser; Melvin Winokur

[57] ABSTRACT

Bisphosphonate, particularly alendronate, can prevent or treat bone loss associated with immunosuppressive therapy, whether or not the immunosuppressive therapy is associated with an organ transplant.

14 Claims, No Drawings

BISPHOSPHONATES PREVENT BONE LOSS ASSOCIATED WITH IMMUNOSUPPRESSIVE THERAPY

SUMMARY OF THE INVENTION

This invention relates to the use of bisphosphonates, particularly alendronate, to prevent bone loss associated with immunosuppressive therapy, and in particular when such therapy is used in conjunction with organ transplantation.

BACKGROUND OF THE INVENTION

Patients suffering fom various medical conditions which require an organ or bone marrow transplant, need a variety of drugs in order to suppress the body's tendency to reject the organ. This generally requires that the patient take one or more immunosuppressive agents, such as cyclosporine or the like, often in combination with adrenal corticosteriods, such as methylprednisolone. Unfortunately, the combination of the underlying condition, immobility or decreased mobility, and drug therapy causes these patients to experience a high degree of bone loss.

Further, various immunosuppressive agents are being tried as therapeutic agents in treating various conditions which do not necessarily involve organ transplantation, such as in rheumatoid arthritis, psoriasis, inflammatory bowel disease and nephrotic syndrome. These patients also are at high risk for bone loss.

It would be desirable to be able to combat or prevent bone loss in patients who are undergoing organ transplants or receiving immunosuppressive therapy in association with an organ transplant or other underlying medical condition.

DETAILED DESCRIPTION OF THE INVENTION

It has been found in accordance with this invention that bisphosphonates can prevent and treat bone loss associated with immunosuppressive therapy when administered either in either a prophylactically or therapeutically effective amount. In particular, alendronate (4-amino-1-hydroxybutylidene-1,1-bisphosphonate) or a pharmaceutically effective salt thereof, can prevent and treat bone loss associated with organ transplants when administered either in either a prophylactically or therapeutically effective amount.

A further aspect of this invention is to prevent or treat bone loss associated with immunosuppressive therapy, regardless of whether the therapy accompanies organ transplantion by administration of an effective amount of a bisphosphonate selected from the group consisting of: alendronate, etidronate (1-hydroxy-ethidene-bisphosphonic acid), pamidronate (3-amino-1-hydroxypropyildiene-1,1-diphosphanate), risedronate (2-(3-pyridinyl)-1-hydroxyethylidene-bisphosphonic acid), clodronate (dichloromethylene-bisphosphonic acid), tiludronate (chloro-4-phenylthiomethylidene-bisphosphonic acid), ibandronic acid (1-hydroxy-3(methylpentylamino)-propylidene-bisphosphonic acid, and pharmaceutically acceptible salts of any of the foregoing, and mixtures of any of the acids and any of the salts. All of the foregoing compounds are well known in the art.

Generally the patient undergoing immunosuppressive therapy in accordance with this invention will be receiving cyclosporine or a similar drug. In addition, the patient may also be receiving prednisone or other corticosteroid.

As used throughout the specification and claims, the following definitions apply:

"Prophylactically effective amount"—the amount of alendronate needed to prevent or lessen the severity of bone loss related to immunosuppressive therapy, regardless of whether the immunosuppressive therapy is accompanied by organ transplantation.

"Therapeutically effective amount"—the amount of alendronate needed to treat bone loss related to immunosuppressive therapy, regardless of whether the immunosuppressive therapy is accompanied by organ transplantation.

In a preferred aspect of this invention, the patient will receive alendronate. Alendronate may be prepared according to any of the processes described in U.S. Pat. Nos. 5,019,651, 4,992,007, and U.S. application Ser. No. 08/286,151, filed Aug. 4, 1994, each of which is hereby incorporated by reference. The pharmaceutically acceptable salts of alendronate include salts of alkali metals (e.g., Na, K), alkaline earth metals (e.g. Ca), salts of inorganic acids, such as HCl and salts of organic acids such as citric acid and amino acids. Sodium salt forms are preferred, particularly the monosodium salt trihydrate form.

Many of the bisphosphonate compounds of the present invention can be administered in oral dosage forms such as tablets, capsules (each of which includes sustained release or timed release formulations), pills, powders, granules, elixirs, paste, tinctures, suspensions, syrups, and emulsions. Likewise they may be administered in an intravenous (bolus or infusion), intraperitoneal, subcutaneous, or intramuscular form, all using forms well known to those of ordinary skill in the pharmaceutical arts. An effective but non-toxic amount of the bisphosphonate compound desired can be used to prevent bone loss.

The dosage regime utilizing the claimed method is selected in accordance with a variety of factors including type, age, weight, sex, and medical condition of the patient; the severity of the condition to be treated; the route of administration; the renal and hepatic function of the patient; and the particular compound or salt thereof employed. An ordinarily skilled physician or clinician can readily determine and prescribe the effective amount of the drug required to prevent and or treat bone loss.

Oral dosages of the present invention when alendronate is the bisphosphonate will range from between 0.05 mg per kg of body weight per day (mg/kg/day) to about 1.0 mg/kg/day. Preferred oral dosages in humans may range from daily total dosages of about 2.5–50 mg/day over the effective treatment period, and a preferred amount is 5, 10 or 20 mg/day.

Alendronate may be administered in a single daily dose or in a divided dose. It is desirable for the dosage to be given in the absence of food, preferably from about 30 minutes to 2 hours prior to a meal, such as breakfast to permit adequate absorption.

In the methods of the present invention, the active ingredient is typically administered in admixture with suitable pharmaceutical diluents, excipients or carriers (collectively referred to herein as "carrier materials") suitably selected with respect to the intended form of administration, i.e. oral tablets, capsules, elixirs, syrups and the like and consistent with conventional pharmaceutical practices. For example, for oral administration in the form of a tablet or capsule, the active ingredient can be combined with an oral, non-toxic, pharmaceutically acceptable inert carrier such as lactose, starch, sucrose, glucose, methyl cellulose, magnesium stearate, mannitol, sorbitol, croscarmellose sodium and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture of active ingredient(s) and inert carrier materials. Suitable binders may include starch, gelatin, natural sugars such as glucose, anhydrous lactose, flee-flow lactose, beta-lactose, and corn sweeteners, natural and synthetic gums, such as acacia, tragacanth or sodium alginate, carboxymethyl cellulose, polyethylene glycol, waxes, and the like. Lubricants used in these dosage forms include sodium oleate, sodium stearate, magnesium sterate, sodium benzoate, sodium acetate, sodium chloride and the like. A particularly preferred tablet formulation for alendronate is that described in U.S. Pat. No. 5,358,941, which is hereby incorporated by reference.

The compounds used in the instant method may also be coupled with soluble polymers as targetable drug carriers. Such polymers can include polyvinylpyrrolidone, pyran co-polymer, polyhydroxylpropyl-methacrylamide and the like.

Patients undergoing immunosuppressive therapy may be male or female of any age. Women may be pre- or postmenopausal.

The following non-limiting examples are presented to better illustrate the invention.

EXAMPLE 1

Alendronate for the Prevention and Treatment of Cyclosporine-induced Bone Loss 220 men and women are enrolled in a clinical study to assess the effectiveness of alendronate to prevent and treat bone-loss associated with immunosuppressive therapy. All subjects are receiving an organ transplant; the majority are receiving a heart, lung or liver transplant. The patients are randomized into 5 groups which receive either placebo, 2.5, 5, 10, or 20 mg/day alendronate for one year, beginning within one week post transplant. In addition to standard amounts of cyclosporine and steroid such as prednisone, all patients also receive 1000 mg per day calcium and 250 IU per day Vitamin D.

Spine and hip bone mineral densities are monitored, and all incidences of fractures are recorded.

After one year, patient receiving alendronate (at any dose) have a statistically significantly higher spine and hip BMD than placebo patients, and have experienced less fractures. This result is obsered in both strata: Those with low starting BMD are seen to gain BMD. Those whose starting BMD is not low are observed to retain BMD. Thus alendronate prevents and treats bone loss associated with immunosuppressive therapy.

What is claimed is:

1. A method of treating or preventing bone loss associated with immunosuppressive therapy comprising: administering an effective amount of a bisphosphonate selected from the group consisting of: 4-amino-1-hydroxybutylidene-1,1-bisphosphonic acid, 1-hydroxy-ethidene-bisphosphonic acid, 3-amino-1-hydroxypropyildiene-1,1-diphosphonate, 2-(3-pyridinyl)-1-hydroxyethylidene-bisphosphonic acid, dichloromethylene-bisphosphonic acid, chloro-4-phenylthiomethylidene-bisphosphonic acid, 1-hydroxy-3(methylpentylamino)-proylidene-bisphosphonic acid, pharmaceutically acceptable salts of any of the foregoing, and mixtures thereof to a patient undergoing immunosuppressive therapy.

2. A method according to claim 1 wherein the patient is receiving immunosuppressive therapy in association with an organ transplant.

3. A method according to claim 2 comprising administering 4-amino-1-hydroxybutylidene-1,1-bisphosphonic acid or a pharmaceutically acceptable salt thereof.

4. A method according to claim 3 wherein the 4-amino-1-hydroxybutylidene-1,1-bisphosphonic acid is in the form of monosodium salt trihydrate.

5. A method according to claim 4 wherein the 4-amino-1-hydroxybutylidene-1,1-bisphosphonic acid is administered in a prophylactically effective amount.

6. A method according to claim 5 wherein the 4-amino-1-hydroxybutylidene-1,1-bisphosphonic acid is administered orally.

7. A method according to claim 5 wherein the 4-amino-1-hydroxybutylidene-1,1-bisphosphonic acid is administered in a dose of from 2.5 to 50 mg per day.

8. A method according to claim 7 wherein the 4-amino-1-hydroxybutylidene-1,1-bisphosphonic acid is administered in a dose of 5 mg, 10 mg, or 20 mg per day.

9. A method of treating bone loss associated with immunosuppressive therapy comprising administering a therapeutically effective amount of 4-amino-1-hydroxybutylidene-1,1-bisphosphonic acid or a pharmaceutically acceptable salt thereof to a patient undergoing immunosuppressive therapy.

10. A method according to claim 9 wherein the 4-amino-1-hydroxybutylidene-1,1-bisphosphonic acid is in the form of monosodium salt trihydrate.

11. A method according to claim 10 wherein the 4-amino-1-hydroxybutylidene-1,1-bisphosphonic acid is administered orally.

12. A method according to claim 10 wherein the 4-amino-1-hydroxybutylidene-1,1-bisphosphonic acid is administered in a dose of from 2.5 to 50 mg per day.

13. A method according to claim 12 wherein the 4-amino-1-hydroxybutylidene-1,1-bisphosphonic acid is administered in a dose of 5 mg, 10 mg, or 20 mg per day.

14. A method according to claim 9 wherein the immunosuppressive therapy is associated with an organ transplant.

\* \* \* \* \*